United States Patent [19]

Miller et al.

[11] Patent Number: 5,325,731
[45] Date of Patent: Jul. 5, 1994

[54] FLUID FLOW AND MOUNTING SYSTEM FOR A SAMPLING PUMP

[75] Inventors: Royce Miller, Liberty; Dale Schafer, Missouri City, both of Tex.

[73] Assignee: Precision General, Inc., Houston, Tex.

[21] Appl. No.: 911,414

[22] Filed: Jul. 10, 1992

[51] Int. Cl.⁵ ................................................ G01N 1/14
[52] U.S. Cl. ................................. 73/863.83; 73/863.86
[58] Field of Search .......... 73/863.83, 863.84, 863.85, 73/863.86

[56] References Cited

U.S. PATENT DOCUMENTS

| | | | |
|---|---|---|---|
| 2,351,764 | 6/1944 | Jarrett | 73/863.85 X |
| 2,693,114 | 11/1954 | Tapp et al. | 73/863.84 X |
| 2,811,041 | 10/1957 | Beatty | 73/863.83 |
| 3,007,340 | 11/1961 | Kraftson | 73/863.85 X |
| 3,090,323 | 5/1963 | Smith | 73/863.83 X |
| 3,401,565 | 9/1968 | Stoll et al. | 73/863.83 X |
| 3,534,613 | 10/1970 | Travor et al. | 73/863.85 |
| 3,625,065 | 12/1971 | Thompson | 73/863.85 X |
| 4,172,670 | 10/1979 | Welker | 73/864.62 X |
| 4,391,152 | 7/1983 | Ellett | 73/863.84 |
| 4,403,518 | 9/1983 | Welker | 73/864.34 |
| 4,470,773 | 9/1984 | Welker | 73/864.62 X |
| 4,525,127 | 6/1985 | Welker | 417/479 |
| 4,531,891 | 7/1985 | Zeck | 417/401 |
| 4,557,151 | 12/1985 | Welker | 73/863.84 |
| 4,628,750 | 12/1986 | Welker | 73/864.63 |
| 4,858,477 | 8/1989 | Wienck | 73/863.54 |
| 4,920,626 | 5/1990 | Nimberger | 29/282 |
| 4,928,536 | 5/1990 | Welker | 73/863.83 |
| 4,942,772 | 7/1990 | Welker | 73/863.83 |
| 5,074,154 | 12/1991 | Allen et al. | 73/864.34 |
| 5,092,742 | 3/1992 | Allen et al. | 417/313 |
| 5,109,709 | 5/1992 | Nimberger | 73/863.84 |

*Primary Examiner*—Tom Noland
*Attorney, Agent, or Firm*—Browning, Bushman, Anderson & Brookhart

[57] ABSTRACT

Improved methods and apparatus for providing a fluid flow and mounting system comprised a mounting nipple, a coupling for threaded engagement with a valve assembly, and a rigid flow line having preselected dimensions. The system of the present invention is particularly adapted for supporting a sampling pump from a pipe line, with the sampling pump including a manifold block having a pair of fluid ports for passing fluid in a hot-loop between the flow line and a sampling pump, and with the valve assembly being mounted to the flow line and including a pair of through passageways. The mounting nipple has a stop surface at each end thereof for engaging the manifold block and valve assembly, respectively, to fix the axial position of the manifold block with respect to the valve assembly. The coupling is rotatable about the mounting nipple for threaded engagement with mating threads on the valve body. With the mounting nipple fixed to the manifold, the sampling pump and mounting nipple may be rotated as an assembly with respect to the valve assembly until the outlet port in the manifold block achieves a preselected position with respect to the inlet port of the return fluid passageway in the valve assembly, and a rigid flow line having preselected dimensions is then used to interconnect these ports.

20 Claims, 2 Drawing Sheets

5,325,731

FLUID FLOW AND MOUNTING SYSTEM FOR A SAMPLING PUMP

FIELD OF THE INVENTION

The present invention relates to methods and apparatus for mounting a fluid sampling system to a storage vessel, and for transmitting fluid in a closed loop between the storage vessel and the sampling system. More particularly, this invention relates to improved techniques for interconnecting a conventional multi-port manifold block of a liquid or gas sampling pump to a valve assembly mounted to a pipe line, with the valve assembly including a pair of flow passageways for transmitting fluid through the closed loop system.

BACKGROUND OF THE INVENTION

Fluid sampling pumps have long been used to take repeated samples from a pipe line or other vessel, and incrementally input sample "bites" into a storage cylinder or similar container, so that the fluid in the cylinder represents a test fluid for determining the characteristics of the fluid stored in the vessel or flowing through the pipe line. The pipe line conventionally includes a threaded side port for sealingly mounting a valve assembly thereto, with a probe extending from the valve assembly into the pipe line for transmitting a sample to the pump. The sampling pump, a pump actuator, a regulator, and an electronic sampling controller are typically housed within a protective housing. Customers of sampling systems prefer a mounting technique whereby the sampling pump and related components within the housing may be mounted directly to the pipe line, thereby reducing installation costs. Various types of liquid or gas sampling pumps, and further background information regarding systems for obtaining fluid samples, are disclosed in U.S. Pat. Nos. 4,172,670, 4,403,518, 4,470,773, 4,525,127, 4,531,895, 4,557,151, 4,628,750 and 5,074,154.

Some prior art sampling pump systems have been connected by flexible tubing or similar flexible conduits to the pipe line, and the sampling pump and enclosure are then not physically supported by the pipe line. Those skilled in the art appreciate that fluid being transmitted in a hot loop from a pipe line to a sampling pump may be under an extremely high pressure, e.g., in excess of 1,500 PSI. Flexible lines which interconnect components and reliably transmit such high pressure fluids are expensive, and are thus generally avoided. When using either flexible tubing or rigid pipe to form the flow lines between the pipe line and the sampling pump, the sampling pump, its enclosure and the related components may be supported by a pedestal or other structure separate from the pipe line, or alternatively may be supported by arms or mounting brackets to the pipe line. The sampling pump system user generally desires to support the sampling pump and enclosure from components which both structurally interconnect the sampling pump to the pipe line and which serve to transmit the fluid from the pipe line to the sampling pump, thereby reducing installation costs. Such users also prefer that the flow line and mounting system have the capability to allow the user to remount an existing conventional pump and enclosure at a new installation site according to the preferred supporting techniques, and without disconnecting the pump or the related equipment within the enclosure in order to remount the pump and enclosure according to this preferred technique to the same or a new pipe line.

Operators of sampling pumps generally prefer to maintain a "hot loop" between the pipe line and the sampling pump. This hot loop allows a slight amount of fluid to flow substantially continuously from the pipe line to a location adjacent the inlet port of the pump, so that the pump is sampling fluid highly representative of fluid flowing through the pipe line at the moment the sample is taken. In a hot loop system, fluid which is not incrementally sampled by the pump is returned to the pipe line. This hot loop system typically employs a manifold block at the base of the pump, with the manifold block being housed within the enclosure and including a pair of ports for fluid communication with the hot loop flow lines. The methods and apparatus of this invention are of the type which desirably provide this hot loop system between the sampling pump and the pipe line to maintain high accuracy for the sampling technique. The present invention is concerned with improved techniques for mounting the sampling pump and relating components to the pipe line, and with techniques which provide both the hot loop flow lines and the structural connection between the pipe line and the sampling pump, while accomplishing these goals in a cost effective manner.

U.S. Pat. No. 4,928,536 discloses a sampling system with a lower body 13 for structurally interconnecting a pump with a pipe line. The mounting system is not adapted for engagement with a conventional sampling pump manifold, is expensive to manufacture, and when installed required modifications to a conventional sampling pump enclosure and/or adaption to the components within the enclosure. U.S. Pat. No. 4,391,152 discloses a complex sampling system which includes a plurality of ball valves, and also is not readily adaptable to standard sampling pump systems with conventional enclosures. The system disclosed in this patent does not provide the desired hot loop path as discussed above, and is apparently supported from a structure independent of the pipe line. U.S. Pat. No. 3,625,065 discloses a sampling system which utilizes flow lines between the sensor and the pipe line, with the flow lines being of a type which cannot reasonably support sampling pumps and related components within the enclosure, as discussed above. U.S. Pat. No. 3,534,613 discloses an early version of sampling system which does not form a reliable seal with the pipe line. Flow passes through flexible tubular member 67, and the system is not the hot-loop type. U.S. Pat. No. 3,007,340 discloses an electrical measurements system with valves 23 and 28 being in fluid communication by the conduit 24. U.S. Pat. No. 2,351,764 discloses a gas sampling system with external pipes and valves for interconnecting ports.

U.S. Pat. No. 5,109,709 discloses a system for mounting a sampling pump and related components within an enclosure to a pipe line while transmitting fluid in a hot loop between the pipe line and the sampling pump. The technique of this patent permits the mounting of the sampling pump and enclosure at one of a plurality of rotational positions, so that the installer may selectively rotate the pump and enclosure with respect to the pipe line when making the interconnection. The plurality of fittings, nipples, and an interface plate connect the valve body fixed to the pipe line and the pump manifold, while transmitting fluid to the pump in the desired hot loop. The technique disclosed in this patent, while highly reliable, is cost prohibitive for many applications due to the machining expense of the fittings, nipples, and interface plate. Moreover, the system disclosed in this patent includes numerous components to provide the desired structural and fluid connection between the pump and the pipe line, and is considered too complex by some sampling pump system users.

U.S. Pat. No. 4,920,626 discloses a device for structurally interconnecting a instrument manifold within an orifice plate assembly. U.S. Pat. No. 4,942,772 discloses a stack sampling system utilizing sampling lines between sampling equipment and a fitting threaded to the stack. U.S. Pat. No. 4,858,477 discloses a flow system for a dry material sample collector. The techniques disclosed in these patents illustrate efforts of companies involved in sampling technology, but do not teach the improved sampling pump mounting technique of the present invention.

The disadvantages of the prior art are overcome by the present invention, and improved methods and apparatus are hereafter disclosed for mounting a sampling pump and related components to the fluid source, such as a pipe line. The mounting technique of the present invention maintains high reliability for the sampling procedure by utilizing a hot-loop flow technique, allows the sampling system user to the reliably install the sampling pump at a desired location without utilizing special tools or specially adapted mounting components, minimizes installation costs, and may be used to re-mount existing sampling pump systems at the same or new installation sites.

SUMMARY OF THE INVENTION

An exemplary embodiment of this invention comprises a mounting nipple, a coupling, and a rigid flow line which together form both the desired structural and fluid connection between a valve assembly mounted to fluid storage vessel and a manifold block for a sampling pump. In a typical installation, the sampling pump manifold block has a pair of lower ports which communicate with apertures provided in the sampling pump enclosure, and which serve as input and output ports for the hot loop fluid circulating between the pipe line and the sampling pump. The pipe includes a sampling pump port having tapered threads, and the valve assembly is mounted to the pipe line with mating tapered threads. The valve assembly includes a fluid input through passageway for transmitting fluid from the pipe line to the manifold block, and a fluid return passageway for transmitting fluid from the manifold block back to the pipe line.

The mounting nipple and coupling provide substantially the entirety of the structural interconnection between the valve assembly and the sampling pump manifold block to support the sampling pump and related components within or attached to the pump enclosure. The mounting nipple has an axial flow path therethrough, with lower end of this flow path being in fluid communication with the fluid input passageway in the valve assembly, and an upper end of this passageway being in fluid communication with the input port in the manifold block. The upper end of the mounting nipple is threaded to a corresponding threaded port in the manifold block, and this upper end also includes a stop surface for engaging the manifold block to fix the axial position of the mounting nipple with respect to the manifold block. The lower end of the mounting nipple has a valve assembly stop surface for engaging the valve assembly to fix the axial position of the mounting nipple with respect to the valve body. The coupling is rotatable about the mounting nipple, and has internal threads for mating engagement with corresponding threads on the valve body. A stop member is provided for limiting axial movement of the coupling away from the upper end of the mounting nipple, so that the axial position of the valve body with respect to the manifold block is fixed when the system components are installed. Since this axial position is fixed, a low-cost rigid flow line may be used for maintaining fluid flow between the output port of the manifold block and the return passageway in the valve body. The lower end of the rigid flow line is connected to a side port in the valve body, and an elbow nipple threaded to the output port of the manifold block allows the use of a substantially U-shaped rigid tube to serve as the return flow line for the hot loop fluid. The apparatus of the present invention thus provides a reliably and relatively inexpensive hot-loop fluid interconnection between the pipe line and a sampling pump, and the same components which provide this hot loop path structurally support the sampling pump and its related components from the pipe line.

According to the method of the invention, the mounting nipple may be fixedly connected to the input port of the manifold block, and the valve assembly threadably connected to the tapered port in the pipe line. With the coupling positioned on the mounting nipple, the sampling pump enclosure and the downwardly protruding mounting nipple may be placed on the valve assembly. Before the coupling is securely tightened, the position of the output port in the manifold block may be adjusted with respect to the fluid flow return passageway in the valve assembly by rotating the sampling pump enclosure with respect to the valve assembly, so that the ends of the rigid flow line may be properly aligned for connection. Once the ends of the rigid flow line are at least partially threaded to their respective mating members, the coupling may be securely tightened to fixedly mount the manifold block to the valve assembly, then the securing members at the ends of the rigid flow line may be securely tightened. In this manner, the rigid flow line effectively acts as an alignment device to properly position the rotational orientation of the manifold with respect to the valve body.

It is an object of the present invention to provide a low-cost yet reliable connection between a fluid storage or transportation vessel, such as a pipe line, and a sampling pump. The connection of the present invention both structurally connects the sampling pump and related components to the vessel, and provides a desired hot loop flow path block and back to the vessel to enhance sampling reliability. The present invention utilizes a special mounting nipple and coupling which provide substantially the entirety of the structural connection required between a valve body and sampling manifold, and also fix with precision the axial spacing between the valve body and the manifold so that a rigid flow line manufactured according to pre-selected dimensions may interconnect the valve body and manifold to complete the hot loop path.

It is a significant feature of this invention that the mounting nipple, coupling, and rigid flow line are able to achieve the desired connection between a conventional valve assembly and a sampling pump manifold block which is housed within the sampling pump enclosure. None of the components within the sampling pump enclosure need to be removed or rearranged in order to utilize this enclosure and its internal components in a sampling system which is re-mounted according to the techniques of the present invention. The cost of the mounting and fluid connection technique is substantially reduced compared to prior art techniques, and the system is highly reliable.

It is an advantage of this invention that costly high pressure flexible flow lines are avoided. Components need not be altered at the installation site, or specially adapted for the installation site. Conventional wrenches or similar tools may be used to complete the installation. A sampling pump and relating components may be reliably mounted utilizing the techniques of the present invention at substantially reduced installation costs. A significant advantage of the techniques according to the present invention is that no components need be provided by the installer to reliably mount a sampling system. All required mounting components may be fabricated without regard to the particular conditions at the installation site, and the components may be provided to the sampling pump system user as a pre-packaged kit. The installation technique is comparatively simple, and is readily suggested to the user from the kit components.

These and further objects, features, and advantages of the present invention will become apparent from the following of the detailed description, wherein reference is made to the figures in the accompanying drawings.

DETAILED DESCRIPTION OF PREFERRED EMBODIMENTS

Figure 1:
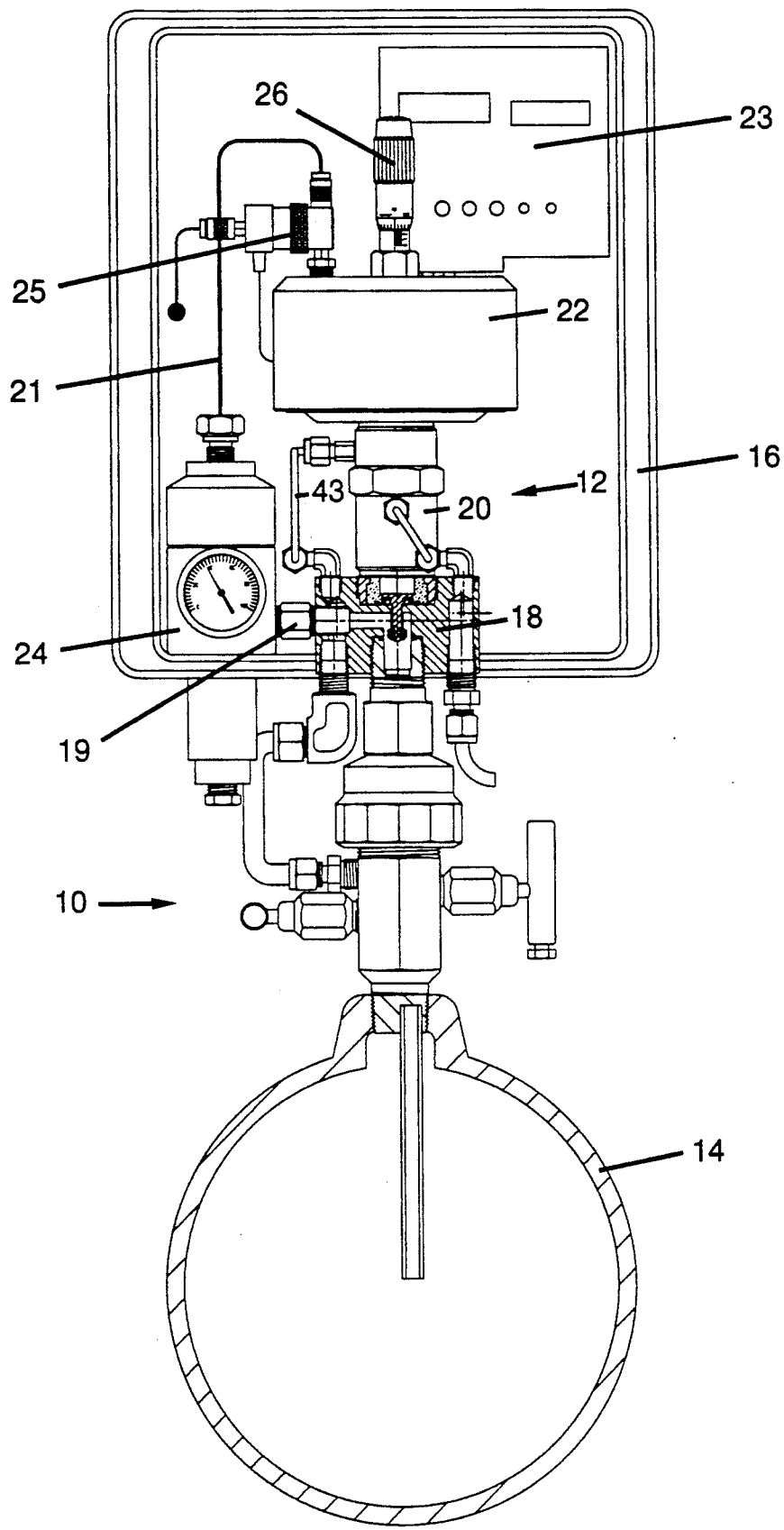
FIG. 1 is a pictorial view, partially in cross-section, of one embodiment fluid sampling pump in a typical application mounted directly to a pipe line according to the present invention.

FIG. 1 depicts fluid flow and mounting system 10 for mounting a sampling pump 12 to a fluid storage or transmission vessel, such a pipe line 14. The pump 12 is conventionally housed within an enclosure 16, and includes a manifold 18 shown in cross-section in FIG. 1 and discussed below in further detail. Pump 12 further comprises a pump body assembly 20, and a pump operator or driver 22. An electronic controller 23 controls sequencing of the sampling pump, and may be either battery or solar powered by a conventional battery pack or solar panel (not shown). Fluid power to the operator is supplied by conducting pressurized media via conduit fitting 19 to pressure reducing regulator 24. Low pressure media, on the order of 30 to 100 PSI, is conducted from regulator 24 via tube 21 to solenoid 25, which is activated by command of controller 23 to deliver low pressure media to pump operator 22. The mounting components 10 enable all components discussed above to be mounted or supported solely by the pipe line 14, and the components either housed within or connected to the enclosure 16.

The protective enclosure 16 conventionally includes a hinged door (not shown) for easy access to set or change the settings on the controller. A feature of this invention is that the enclosure 16 and the components housed therein or secured thereto may be disconnected from an existing pipe line, and re-connected utilizing the mounting components 10 of this invention. A sampling pump enclosure and its related components which are not directly supported from a pipe line may thus be removed from that system, and may be remounted according to the techniques of the present invention so that the enclosure is supported solely by the pipe line. This reconnection operation desirably may be accomplished without removing any components from the enclosure.

Fluid to be sampled by the pump 12 is input to the manifold 18 from the pipeline 14 by the fluid flow and mounting mechanism 10. Fluid flow through the manifold is nominal compared to fluid flow through the pipe line 14, and most fluid entering the manifold 18 exits the manifold and returns to the line 14. A very small percentage of a fluid passing through the line 14 is thus withdrawn by pump 12 and input to a sample vessel (not shown) for subsequent analysis. To maintain high sampling reliability, fluid continually flows in a "hot loop" through the mounting system 10 and the manifold 18 to a location closely adjacent an inlet valve to the pump. The amount of fluid sampled with each pump stroke may be closely controlled by caliper mechanism 26. Further details with respect to the sequencing an operation of a sampling pump are disclosed in U.S. Pat. Nos. 4,531,895 and 5,092,742, each of which are hereby incorporated by reference.

Figure 2:
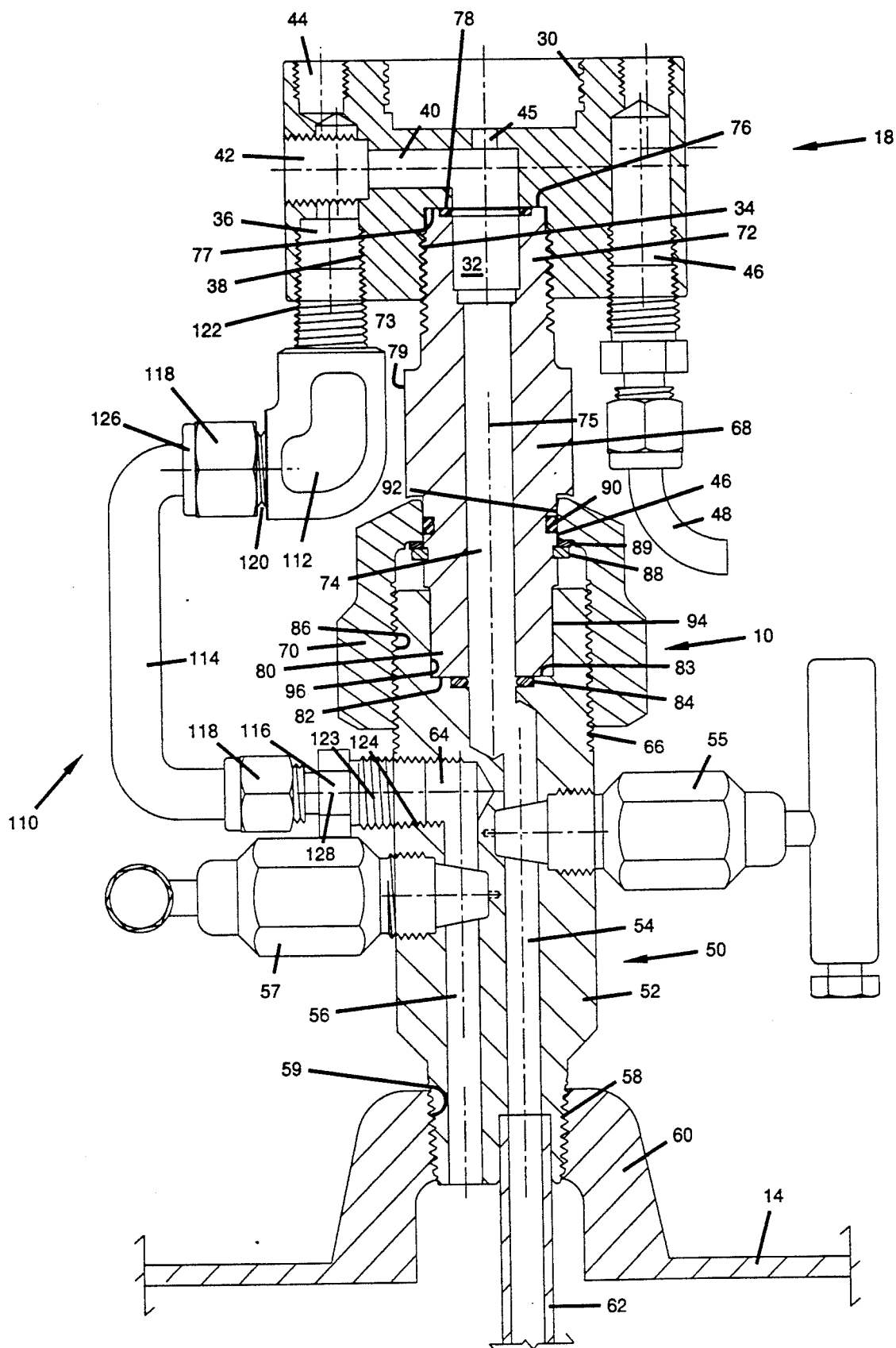
FIG. 2 is a more detailed, partially in cross-section, illustrating a manifold portion of a sampling pump and the components which interconnect a sampling pump to the pipe line.

FIG. 2 depicts in greater detail the sampling pump manifold 18 generally shown in FIG. 1. Manifold 18 may be threadedly connected directly to the pump body 20 by threads 30. The manifold 18 includes a fluid input port 32 formed with straight (non-tapered) threads 34, and a fluid output port 36 defined by tapered or NPT threads 38. Fluid normally flows through the hot loop passage 40 between the fluid input port and the fluid output port. A line (not shown in FIG. 2) may be connected to port 42 and extend to the regulator 24 to power the sampling pump, or this port 42 may optionally be plugged. Port 44 in the manifold 18 is threaded for receiving a conduit (not shown) to establish pipe line pressure to a side port in the pump body. Fluid withdrawn by the sampling pump thus flows through passageway 45. The passageway 46 in the manifold block transmits fluid discharged from the sampling pump to storage transmission line 48, which interconnects the manifold block to a sample container (not shown). Further features with respect to the sampling pump manifold, including details with respect to the sampling pump inlet and strainer which may be contained within the manifold block, are disclosed in U.S. Pat. No. 5,092,742. FIG. 2 also depicts probe valve assembly 50, which comprises a valve body 52 having a fluid input through passageway 54 and a fluid return through passageway 56. Conventional valves 55 and 57 are mounted to the valve body for controlling fluid flow through each of the respective passageways. The lower end of body 52 includes tapered or NPT threads 58 for sealingly mating with similar tapered threads 59 provided within the sampling neck 60 in the side of the pipe line 14. A sampling probe 62 provides fluid communication between the passageway 54 and the interior of the line 14. The passageways 54 and 56 are thus substantially in parallel within the body 54, although passageway 54 discharges through the top of the valve body 52, while passageway 56 receives return hot loop fluid through side port 64 in the valve body. The upper end of the valve body includes straight (non-tapered) external thread 66.

Mounting nipple 68 and coupling 70 together provide substantially the entirety of the structural connection between the valve body and the sampling pump manifold, and thus between the line 14 and the sampling pump 12. The sampling pump end 72 of nipple 68 includes straight (non-tapered) external threads 73 for mating engagement with similar threads 34 in the manifold 18. Through passageway 74 in the mounting nipple is formed about a central axis 75, and provides a fluid connection between the flow passageway 54 in the valve body and the input port 32 in the manifold 18. The mounting nipple 68 includes a stop surface 76, which in the embodiment depicted is an end surface, for engaging a corresponding stop surface 77 on the manifold 18, thereby fixing the position of the nipple 68 with respect to manifold 18 along the axis 75. The conventional elastomeric seal 78 is provided for maintaining static sealing engagement between the manifold 18 and the nipple 68. In order to securely thread the nipple 68 to the manifold for both maintaining a reliable seal and to fix the axial position of the mounting nipple with respect to the manifold, external surface 79 of the fitting may be shaped hexagonally or otherwise shaped to receive a conventional torquing tool. The opposing valve assembly end 80 of the mounting nipple 68 similarly provided with a stop surface 82 for engaging the stop surface 83 on the valve body 52 and thereby fix the axial position of the mounting nipple with respect to the valve body. Another elastomeric O-ring 84 is provided for maintaining a reliable static seal between the nipple 68 and the valve body.

Coupling 70 has a nut-like configuration, and includes straight threads 86 for mating engagement with threads 66 on the valve body. Nut 70 can rotate freely with respect to the mounting nipple 68, although axial movement of the nut 70 away from the end 72 of the mounting nipple is limited by stop member 88, which consists of a snap-ring fitted within a groove in the nipple. A back-up ring 89 may be provided between the coupling 70 and snap-ring 88. A seal 90 is provided for sealing between the mounting nipple and the inner cylindrical surface 92 of the coupling 70, although this seal 90 merely serves to cooperate with the threads 66, 86 to provide protection from the elements exterior of the sampling system, and need not provide a fluid-tight pressurized seal. The lower valve assembly end 80 of the mounting nipple has a cylindrical external surface 94 which has a diameter only slightly smaller than the internal cylindrical surface 94 in the upper end of the valve body 52. These mating cylindrical surfaces permit little (no discernable) pivotal movement of the mounting nipple 68 once installed on the valve assembly 50. Also, cylindrical surface 94 on the nipple 68 is only slightly smaller in diameter than internal cylindrical surface 96 on the coupling 70, so that the threads 86 remain properly aligned with the threads 66 to ensure that a uniform circumferential pressure is applied to rigidly mount the nipple 68 and thus the sampling pump to the valve 52 and thus the pipe line 14.

Passageways 54, 74 and 40 thus provide the flow path from the line 14 to the sampling pump 12, while rigid (non-flexible) line 110 provides the returned flow path for the hot loop fluid by interconnecting the port 36 in the manifold 18 with the port 64 in the valve assembly 50, and thus the passageway 56 in the valve body 52. Line 110 in turn comprises an elbow nipple 112, a rigid flow conduit 114, and straight nipple 116. A coupling nut 118 is provided at each opposing end of the conduit 114, and screws on straight threads 120 for mating engagement in the respective nipples 112, 116. Torqued engagement of each nut 118 causes a ferrule (not shown) to form a reliable high pressure metal-to-metal fluid-tight seal in a conventional manner between the end of the conduit 114 and the respective fitting. Alternatively, the ends of the conduit 114 may be flared so that respective nuts or other conventional securing members form a fluid-tight metal-to-metal seal between the flared end of the tubing and the respective nipples.

The fitting 112 includes tapered or NPT threads 122 for sealing engagement with similar threads 38 provided about the port 36 in the manifold. The fitting 112 desirably extends upward through the enclosure 16 shown in FIG. 1 for mating engagement with the manifold block while positioned within the enclosure. Similar tapered threads 123 provide sealing engagement with the threads 124 about the side port 64 in the valve body 52. The opposing ends of each of the nipples, being the ends which are in engagement with the conduit 114, each preferably have central axis 126 and 128 lying within parallel planes, which may each be perpendicular to the axis 75 of the mounting nipple. This configuration allows the rigid conduit 114 to desirably have a substantially U-shaped configuration, with the ends of the conduit 114 being formed about axes which are substantially parallel. This feature substantially minimizes the difficulties associated with installing the sampling pump according to the present invention, as explained subsequently.

According to the method of the present invention, mounting nipple 68 may be threaded to the manifold 18 so the surfaces 76 and 77 engage, thereby fixing the axial position of the mounting nipple with respect to the manifold, and simultaneously forming a fluid-tight seal between these components with the O-ring 78. Assuming the sampling pump is within a conventional enclosure 16, the mounting nipple at this stage will extend downward through a suitable opening provided in the enclosure 16 which houses the components shown in FIG. 1. Also, a probe valve assembly 50 may be threaded to the pipe line 14, with the valves 55 and 57 already mounted to the valve body. Elbow nipple 112 may also be securely connected to the manifold 18, and straight nipple 116 may be similarly threaded to valve body 52 (or nipple 116 may have been connected to the valve body before being shipped to the installation site). With the mounting nipple 68 extending downward from the enclosure, the enclosure 16 may be positioned so that stop surface 82 on the mounting nipple "lands" on surface 83 on the valve body, and the coupling 70 may then be loosely tightened to prevent the enclosure from falling off the valve body. The sampling pump and enclosure may then be rotated until the nipples 112 and 116 are positioned approximately where they need to be in order for the ends of the rigid conduit 114 to make up with each of these nipples. The proper end of the conduit 114 may be loosely connected to its respective nipple by rotating a respective coupling nut 118 and, if necessary, further rotational adjustment of the enclosure made so that the opposing end of the conduit is aligned with its respective nipple. Since the coupling 70 has not yet been tightened, the enclosure may freely rotate with respect to the valve assembly 50. Once the connection is made between each end of the tubing 114 and each of the respective fittings 112 and 116, the coupling 70 and the coupling nuts 118 may each be tightened to the desired extent. It may be seen that the conduit 114 serves as a alignment device or template to assist in properly positioning the rotational orientation of the manifold 18 with respect to the valve body 52, since the connections between the ends of the conduit 114 and the fittings 112 and 114 can only be made up when this rotational alignment is proper.

The technique as described above provides a reliable mounting system and hot loop fluid connection between a fluid storage or transportation vessel and a sampling pump. The rigid conduit may be manufactured according to preselected dimensions, since the spacing between the outlet port of the manifold and the inlet port of the return passageway to the valve assembly is fixed, and since the manifold and sampling pump enclosure may be selectively rotated for proper alignment of components before the mounting nipple is rigidly connected to the probe valve assembly. In most case, the outlet port of the manifold block will not be positioned directly above the inlet port and return passageway in the valve assembly. Nevertheless, since the positions of these ports relative to each other is preselected before the system is installed at a particular site, the rigid flow line may be manufactured according to preselected dimensions. It should be understood that the term "rigid" when used with respect to the flow line is intended to refer to a conduit or similar flow transmission device which is conventionally considered rigid or non-flexible, to differentiate such devices from flexible tubing, hose, and other flexible conduits which are intentionally designed to be sufficiently flexible to allow appreciable bending of the line at the installation site to achieve the desired connection. The rigid line of the present invention may thus be manufactured from steel or other tubing material which can withstand high pressure and has a relatively low cost, and such rigid tubing should be distinguished, for example, from flexible copper tubing which is intended to be bent to its desired configuration at the installation site. Nevertheless, it should also be understood that a very limited amount flexing of even steel tubing may occur during installation, and since almost every material is slightly flexible, it should be understood that slight flexing of a rigid material is not outside the scope of the present invention. The key to the concept of a rigid flow line according to the present invention is that the precise dimensions of the flow line may be preselected without regard to the installation site, and the concepts of the present invention then used to position the flow line connection port so that they will be in alignment for receiving the ends of the rigid tubing.

The use of elbow nipple 112 allows the conduit 114 to be U-shaped (rather than L-shaped). Very limited flexing of the parallel legs of the conduit 114 permits slight variations for making up connections, since the axial position of the nipple 112 may vary slightly with respect to the valve assembly 50 as a result of using tapered threads for engagement of this nipple with the manifold block. The U-shaped tubing 114 permits substantially easier assembly of the flow path and mounting components 10 than would be obtained if the manifold end of the rigid conduit were moved axially upwardly to form a connection to the manifold. It is desirable that the tubing 114 extend radially outward from the mounting nipple no farther than necessary. In order to permit slightly greater tolerance variations and/or easier assembly, the U-shaped conduit 114 could be fabricated with slightly longer substantially parallel legs, thereby positioning the "base" of the U-shaped conduit radially further outward from the mounting nipple.

The stop surfaces 76 and 82 on the mounting nipple preferably each lie within a plane substantially perpendicular to the axis 75 of the mounting nipple, and accordingly their mating surfaces 77 and 83 on the manifold and valve body, respectively, similarly lie within planes substantially perpendicular to the central axis of the mounting nipple. While it is feasible that these stop surfaces could have a different configuration, e.g., slightly frustoconical, the technique as described above reduces manufacturing costs and achieves the objective of limiting axial movement of the components relative to each other.

A preferred technique for securing the mounting nipple to the manifold block is the use of threads 34, 73 as described herein, and a preferred technique for sealing these components is the elastomeric seal 78. It should be understood that other securing members could be used to structurally lock the position of these components together, and other conventional sealing members could be used for maintaining the sealing engagement of these components under high pressure. It is a feature of the invention, however, that the components which structurally connect the mounting nipple to the manifold block are separate from the components used to seal between the mounting nipple and manifold block. Tapered threads could theoretically be used to both structurally connect and seal between the mounting nipple and manifold block, but the use of tapered threads would normally introduce axial variation between the position of the mounting nipple with respect to the manifold block, which is not desired. Similarly, various securing mechanisms and sealing mechanisms could be used to structurally interconnect and seal the lower end of the mounting nipple to the valve assembly. Again, it is a feature of the present invention that these functions be provided by separate components, and it is particularly cost effective to use a conventional O-ring 84 to sealingly engage these components. The combination of stop member 88, coupling 70 and engaging threads 86, 66, in conjunction with the close-fit of cylindrical surfaces 96, 94, is a preferred technique for structurally interconnecting the mounting nipple and the valve body, although other securing members could be used.

As noted above, the cylindrical surfaces 96, 94 substantially limit any pivotable movement of the mounting block and thus the sampling pump with respect to the valve assembly, and each of these surfaces preferably has an axial length of at least one centimeter to achieve this objective. The planar stop surfaces 83, 82 fix the axial position of the mounting nipple and thus the sampling pump with to the valve block, while the snap ring 88 and the threaded coupling lock this axial position in place and provide additional structural support between the valve assembly and mounting nipple.

Various further modification will be suggested from the foregoing disclosure. The pump manifold could be provided so that the fluid output port was spaced between the fluid input port and the sample passageway, so that fluid would flow in a hot loop through the valve body and out a side port, then through a rigid conduit and to the manifold, and be returned through the mounting nipple and a return passageway in the valve body. Various alternate arrangements could be provided for achieving the objective of fixing the axial position of the manifold with respect to the mounting nipple, and for fixing the mounting nipple with respect to the valve body. A nut and stabilizer foot arrangement, as disclosed in U.S. Pat. No. 4,920,626, could be used to replace the threaded connection between the valve body and pipe line 14.

The disclosure and description of the invention are thus illustrative and explanatory thereof, and various other changes in the size, shape, and materials, as well as the details of the illustrated construction and method of assembly, may be made within the scope and spirit of the invention, which should be understood to be defined of the claims which follow.

What is claimed is:

1. A hot loop fluid flow and mounting system for supporting a sampling pump from a pipe line having a sampling port, the sampling pump including a manifold block having a pair of fluid ports for passing fluid into and out of the manifold block, and a valve assembly mounted to the pipe line sampling port and including a pair of through passageways in a valve body for transmitting fluid from the pipe line to the manifold block, and for returning fluid from the manifold block to the pipe line, the system comprising:

a mounting nipple having an axial flow path therethrough, a valve assembly end of the mounting nipple positioning the flow path in fluid communication with one of the pair of through passageways in the valve assembly, and an opposing manifold end of the mounting nipple positioning the flow path in fluid communication with one of the pair of fluid ports in the manifold block;

the manifold end of the mounting nipple including a first securing member for structural engagement with the manifold block, and further including a manifold stop surface for engaging the manifold block to fix the axial position of the mounting nipple with respect to the manifold block;

the valve assembly end of the mounting nipple including a valve assembly stop surface for engaging the valve assembly to fix the axial position of the mounting nipple with respect to the valve body, such that the axial position of the valve body is fixed with respect to the manifold block;

a first seal for maintaining static sealing engagement between the manifold block and the mounting nipple;

a second seal for maintaining static sealing engagement between the mounting nipple and the valve body;

a coupling axially movable with respect to the mounting nipple and having a second securing member for structural engagement with the valve body; and a rigid flow line for transmitting fluid between the other of the pair of ports in the manifold block and the other of the through passageways in the valve assembly, one end of the rigid flow line being structurally connected to a side port in the valve body and an opposing end of the rigid flow line being structurally connected to the other port in the manifold block.

2. The system as defined in claim 1, further comprising:

a stop member on the mounting nipple for limiting axial movement of the coupling away from the manifold end of the mounting nipple.

3. The system as defined in claim 2, further comprising:

a pump end of the valve body having straight external threads;

the coupling is rotatable about the mounting nipple;

the second securing member on the coupling includes internal straight threads for mating engagement with the external straight threads on the valve body.

4. The system as defined in claim 1, further comprising:

the one of the pair of ports in the manifold block is a threaded port having internal straight threads;

the first securing member on the mounting nipple includes straight external threads for mating engagement with the threaded port in the manifold block.

5. The system as defined in claim 1, wherein:

the manifold stop surface on the mounting nipple for engaging the manifold block lies within a plane substantially perpendicular to the axis of the mounting nipple; and the valve assembly stop surface on the mounting nipple for engaging the valve assembly lies within another plane substantially perpendicular to the axis of the mounting nipple.

6. The system as defined in claim 1, further comprising:

the valve body includes a cylindrical-shaped recess for receiving the valve assembly end of the mounting nipple; and the valve assembly end of the mounting nipple has a cylindrical outer surface for close-fit engagement with the cylindrical-shaped recess in the valve body.

7. The system as defined in claim 1, wherein:

the one of the pair of through passageways within the valve assembly is a fluid input passageway for transmitting fluid from the pipe line to the manifold block, and the other of the pair of through passageways is a fluid return passageway for transmitting fluid from the valve manifold to the pipe line;

the one of the pair of ports in the manifold block is a fluid input port, and the other of the part of ports in the manifold block is a fluid output port; and the valve assembly includes a pair of valves, each of the pair of valves being mounted for selectively controlling fluid flow through a respective one of the pair of through passageways.

8. The system as defined in claim 1, further comprising:

the rigid flow line including a rigid conduit; and the one end of the rigid flow line including a valve body nipple for sealing engagement with the side port in the valve body, and a coupling nut for mating with the valve body nipple to sealingly connect a corresponding end of the rigid conduit with the valve body nipple.

9. The system as defined in claim 8, further comprising:

the opposing end of the rigid flow line including a manifold nipple for sealingly engagement with the manifold body, the manifold nipple having a rigid conduit end with a port axis substantially perpendicular to a manifold end port axis of the manifold nipple, and another coupling nut for mating with the manifold body nipple to sealingly connect a corresponding opposing end of the rigid conduit with the manifold body nipple.

10. The system as defined in claim 1, wherein:

the manifold block further includes a sample fluid through passageway for transmitting fluid from the sampling pump to a sampling container, the one of the pair of fluid ports in the manifold block is an input port, and the other of the pair of ports in the manifold block is an output port spaced opposite the sample fluid through passageway with respect to the input port.

11. A fluid flow and mounting system for supporting a sampling pump manifold block from a pipe line, the manifold block having a pair of fluid ports for passing fluid into and out of the manifold block, the system comprising:

a valve assembly including a valve body having a pair of through passageways for transmitting fluid from the pipe line to the manifold block and for returning fluid from the manifold block to the pipe line, and at least one valve for controlling fluid flow through a respective one of the pair of through passageways;

a manifold end of the valve body having straight external threads;

a mounting nipple having an axial flow path therethrough, a valve assembly end of the mounting nipple positioning the flow path in fluid communication with one of the pair of through passageways in the valve assembly, and an opposing manifold with one of the mounting nipple positioning the flow path in fluid communication with one of the pair of fluid ports in the manifold block;

the manifold end of the mounting nipple including a securing member for structural engagement with the manifold block, and further including a manifold stop surface for engaging the manifold block to fix the axial position of the mounting nipple with respect to the manifold block;

the valve assembly end of the mounting nipple including a valve assembly stop surface for engaging the valve body to fix the axial position of the mounting nipple with respect to the valve body, such that the axial position of the valve body is fixed with respect to the manifold block;

a first seal for maintaining static sealing engagement between the manifold block and the mounting nipple;

a second seal for maintaining static sealing engagement between the valve body and the mounting nipple;

a coupling rotatable with respect to the mounting nipple and having internal straight threads for structural engagement with the external straight threads on the valve body; and a flow line structurally independent of the mounting nipple for transmitting fluid between the other of the pair of ports in the manifold block and the other of the through passageways in the valve assembly.

12. the system as defined in claim 11, further comprising:

a stop member for limiting axial movement of the coupling away from the manifold end of the mounting nipple; and the manifold stop surface and the valve assembly stop surface on the mounting nipple each lying within a respective plane substantially perpendicular to the axis of the mounting nipple.

13. The system as defined in claim 11, further comprising:

the one of the pair of ports in the manifold block is a threaded port having internal straight threads; and the first securing member on the mounting nipple includes straight external threads for mating engagement with the threaded port in the manifold block.

14. The system as defined in claim 11, wherein:

the valve assembly end of the mounting nipple has a cylindrical outer surface for close-fit engagement within a cylindrical recess in the valve body.

15. The system as defined in claim 11, further comprising:

the flow line including a rigid conduit;

one end of the flow line including a rigid valve body nipple for sealing engagement with the other through passageway in the valve body and a coupling nut for mating engagement with the valve body nipple to sealingly connect a corresponding end of the rigid conduit with the valve body nipple; and an opposing end of the flow line including a substantially right angle rigid manifold nipple for sealing engagement with the other port in the manifold block, and another coupling nut for mating engagement with the manifold nipple to sealingly connect a corresponding opposing end of the rigid conduit with the manifold body nipple.

16. A method of mounting a sampling pump from a pipe line having a sampling port while providing fluid flow to the sampling pump, the sampling pump including a manifold block having a pair of fluid ports for passing fluid into and out of the manifold block, and a valve assembly mounted to the pipe line sampling port and including a pair of passageways for transmitting fluid from the pipe line to the manifold block and for returning fluid from the manifold block to the pipe line, the method comprising:

(a) sealingly fixing a mounting nipple having an axial flow path therethrough to one of the pair of fluid ports in the manifold block, while engaging a manifold stop surface on the mounting nipple with the manifold block to fix the axial position of the mounting nipple with respect to the manifold block;

(b) positioning the sampling pump and the mounting nipple, the mounting nipple being fixed to the sampling pump, to engage a valve assembly stop surface on the mounting nipple with the valve assembly to position the mounting axially with respect to the valve assembly;

(c) selectively rotating the sampling pump and mounting nipple with respect to the valve assembly until the other of the pair of ports in the manifold block is at a preselected position with respect to the other of the through passageways in the valve assembly;

(d) fixedly securing the mounting nipple to the valve assembly to lock the selected rotational position of the sampling pump and mounting nipple with respect to the valve assembly and to fix the axial position of the mounting nipple with respect to the valve assembly; and (e) mounting a rigid flow line having preselected dimensions between the other of the pair of ports in the manifold block and the other of the through passageways in the valve assembly.

17. The method as defined in claim 16, wherein step (a) includes:

positioning an elastomeric seal for maintaining static sealing engagement between the manifold block and the mounting nipple;

threading the mounting nipple to a corresponding threaded port in the manifold block to structurally interconnect the manifold block and the mounting nipple.

18. The method as defined in claim 16, wherein step (c) includes:

utilizing the rigid flow line as a template to selectively position the other of the pair of ports in the manifold block with respect to the other of the through passageways in the valve assembly.

19. The method as defined in claim 16, wherein step (d) includes:

positioning an elastomeric seal for maintaining static sealing engagement between the mounting nipple and the valve body;

limiting the axial movement of a coupling rotatable about the mounting nipple; and threadably connecting the coupling and the valve assembly to fix the position of the mounting nipple with respect to the valve assembly.

20. The method as defined in claim 16, wherein the rigid flow line comprises a rigid conduit having a substantially U-shaped configuration, and step (e) includes:

securing an elbow nipple to the other of the pair of ports in the manifold block, such that an axis of an outlet port in the elbow nipple lies within a plane substantially parallel to an inlet port in the other of the pair of through passageways in the valve assembly; and securing the rigid conduit having the substantially U-shaped configuration to the elbow nipple and to the inlet port to the other of the pair of through passageways in the valve assembly, such that substantially parallel legs of the U-shaped conduit are aligned for respective engagement with the outlet port in the elbow nipple and the inlet port to the other of the pair of through passageways in the valve assembly.

* * * * *

UNITED STATES PATENT AND TRADEMARK OFFICE
CERTIFICATE OF CORRECTION

PATENT NO. : 5,325,731
DATED : July 5, 1994
INVENTOR(S) : Miller et al.

It is certified that error appears in the above-indentified patent and that said Letters Patent is hereby corrected as shown below:

In column 12, line 42, change "part" to --pair--.

In column 13, line 28, delete "with one" and insert therefor --end--.

Signed and Sealed this

Sixth Day of February, 1996

Attest:

BRUCE LEHMAN

*Attesting Officer*  *Commissioner of Patents and Trademarks*